United States Patent
Khan et al.

(10) Patent No.: US 10,080,712 B2
(45) Date of Patent: *Sep. 25, 2018

(54) ANTI-TATAR ORAL CARE COMPOSITIONS PROVIDING CRYSTALLISATION PREVENTION

(71) Applicant: The Procter & Gamble Company, Cincinnati, OH (US)

(72) Inventors: Golam Faruque Khan, Loveland, OH (US); William Michael Glandorf, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/932,943

(22) Filed: Nov. 4, 2015

(65) Prior Publication Data

US 2016/0120777 A1 May 5, 2016

Related U.S. Application Data

(60) Provisional application No. 62/074,861, filed on Nov. 4, 2014.

(30) Foreign Application Priority Data

Dec. 18, 2014 (EP) .................................... 14198821
Sep. 28, 2015 (EP) .................................... 15187091

(51) Int. Cl.
*A61K 8/24* (2006.01)
*A61K 8/21* (2006.01)
*A61Q 11/00* (2006.01)

(52) U.S. Cl.
CPC ................. *A61K 8/24* (2013.01); *A61K 8/21* (2013.01); *A61Q 11/00* (2013.01)

(58) Field of Classification Search
None
See application file for complete search history.

(56) References Cited

U.S. PATENT DOCUMENTS

| | | |
|---|---|---|
| 2,941,926 A | 6/1960 | Salzmann et al. |
| 3,535,421 A | 10/1970 | Briner et al. |
| 3,678,154 A | 7/1972 | Widder et al. |
| 3,737,533 A | 6/1973 | Moon et al. |
| 3,927,201 A | 12/1975 | Baines et al. |
| 3,927,202 A | 12/1975 | Harvey et al. |
| 3,959,458 A | 5/1976 | Agricola et al. |
| 3,988,433 A | 10/1976 | Benedict |
| 4,136,163 A | 1/1979 | Watson et al. |
| 4,138,477 A | 2/1979 | Gaffar |
| 4,244,931 A | 1/1981 | Jarvis et al. |
| 4,247,526 A | 1/1981 | Jarvis et al. |
| 4,323,551 A | 4/1982 | Parran |
| 4,459,425 A | 7/1984 | Amano et al. |
| 4,515,772 A | 5/1985 | Parran, Jr. et al. |
| 4,661,341 A | 3/1987 | Benedict et al. |
| 4,684,517 A | 8/1987 | Clipper et al. |
| 4,775,525 A | 10/1988 | Pera |
| 4,822,599 A | 4/1989 | Mitra |
| 4,847,070 A | 7/1989 | Pyrz et al. |
| 4,885,155 A | 12/1989 | Parran et al. |
| 5,015,467 A | 5/1991 | Smitherman |
| 5,180,576 A | 1/1993 | Winston et al. |
| 5,180,577 A | 1/1993 | Polefka et al. |
| 5,338,537 A | 8/1994 | White, Jr. |
| 5,451,401 A | 9/1995 | Zerby et al. |
| 5,538,714 A | 7/1996 | Pink et al. |
| 5,622,689 A | 4/1997 | Lukacovic |
| 5,670,138 A | 9/1997 | Venema et al. |
| 5,695,745 A * | 12/1997 | Barton ............ A61K 8/24 424/49 |
| 5,849,271 A | 12/1998 | Lukacovic |
| 2010/0055052 A1 | 3/2010 | Berta et al. |

FOREIGN PATENT DOCUMENTS

| | | |
|---|---|---|
| DE | 3942644 | 2/1991 |
| EP | 0 097-476 * | 4/1984 |
| EP | 0309414 A2 | 3/1989 |
| EP | 0297211 A2 | 4/1989 |
| EP | 0483111 A2 | 4/1992 |
| GB | 741315 | 11/1955 |
| WO | WO9319728 | 10/1993 |

OTHER PUBLICATIONS

U.S. Appl. No. 14/932,927, filed Nov. 4, 2015, Golam Faruque Khan et al.

"Pyrophosphate and Hexametaphosphate Effects in Vitro Calculus Formation", Arch. Oral Biol., vol. 15, pp. 893-896, (1970).

* cited by examiner

*Primary Examiner* — Celeste A Roney
(74) *Attorney, Agent, or Firm* — Parker D. McCrary; James E. Oehlenschlager

(57) ABSTRACT

An oral composition is provided comprising at least 0.5% by weight of the composition of pyrophosphate in an orally acceptable carrier, wherein the pyrophosphate is provided by a mixture of disodium pyrophosphate and tetrapotassium pyrophosphate in a ratio from disodium pyrophosphate to tetrapotassium pyrophosphate in the range of from 1:0.4 to 1:1.2 and wherein the pH value of the composition is in the range of from 6.0 to 8.0. The oral composition can be used for prevention and control of tartar and/or calculus formation.

18 Claims, No Drawings

ANTI-TATAR ORAL CARE COMPOSITIONS PROVIDING CRYSTALLISATION PREVENTION

TECHNICAL FIELD

The present invention relates to mouthwash or mouthrinse oral care compositions, with anti-tartar and anti-calculus effects, wherein said oral compositions comprise pyrophosphates as active agents. In addition, said oral compositions are stable against crystal formation in solution even if the product was frozen and thawed up again.

BACKGROUND OF THE INVENTION

Oral care products such as dentifrice and mouthwash are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, or essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression which can be broadly characterized as mouth feel aesthetics. Calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of certain oral products containing ingredients that promote staining, such as chlorhexidine and stannous salts.

While the art has addressed some of the formulation issues of oral care products relating to cosmetic benefits, there continues to be a need in stain prevention and anti-calculus formation from products for daily use such as dentifrice and mouthwash. The tooth structures that are generally responsible for presenting a stained appearance are enamel, dentin, and the acquired pellicle. Extrinsic staining of the acquired pellicle can arise as a result of compounds, such as tannins and other polyphenolic compounds that have become trapped in and tightly bound to the proteinaceous layer on the surface of the teeth. Discoloration from this type of staining can usually be removed by mechanical methods of tooth cleaning.

In contrast, intrinsic staining occurs when the staining compounds penetrate the enamel and even the dentin, or alternatively, such staining arises from sources within the tooth. Discoloration from intrinsic staining is not readily amenable to mechanical methods of tooth cleaning. Chemical methods, which utilize substances that can penetrate into the tooth structure, are usually required to eliminate such discoloration. Thus, for oral care products for daily use such as dentifrice and mouthwash to provide overall cleaning, it is necessary to add ingredients for provision of antiplaque and anticalculus benefits as well as stain removal and stain control. Such ingredients for removal and control of stain and calculus include abrasives for mechanical cleaning and bleaches, surfactants and chemical chelants for chemical cleaning. Dental abrasives provide important whitening benefits, particularly on 'brushed' areas of teeth, but unfortunately are of limited effect in controlling aesthetically undesirable stains that form along the gumline and interproximally. The stain is mechanically abraded through the use of abrasives or polishing agents normally employed in toothpaste preparations. Bleaches such as urea peroxide, hydrogen peroxide or calcium peroxide, represent the most common forms of whitening agents for teeth. It is believed that peroxides whiten teeth by releasing hydroxyl radicals capable of breaking down the plaque/stain complex into a form that can be flushed away or removed by an abrasive. However, bleaches added to dentifrice and mouthwash, are typically present in low concentrations due to stability and safety limits unique to these product types. At these low concentrations, bleaches which are oxidizing agents have not generally been effective at tooth whitening and stain control. Bleaches and abrasives do not functionally act to prevent acquisition of stains. Abrasive use can reduce rates of stain acquisition by daily removal of newly acquired stains, but this action is a 'treatment' for existing stain, not a preventive chemical action.

Chelants have been suggested in the art for the purpose of retarding calculus formation and removing calculus after it is formed. The chemical approach to calculus inhibition generally involves chelation of calcium ion and/or crystal growth inhibition which prevents the calculus from forming and/or breaks down mature calculus by removing calcium. In addition, chemical chelants can in principle remove stains by binding to teeth surfaces thereby displacing color bodies or chromagens that cause staining. The retention of these chelants can also prevent stains from accruing due to disruption of binding sites of color bodies on tooth surfaces. A number of agents with chelating properties for use in controlling plaque, calculus and stain have been disclosed in the art. For example, ethylenediaminetetraacetic acid, nitrilotriacetic acid and related compounds are disclosed in British Patent 490,384, Feb. 15, 1937; polyphosphonates in U.S. Pat. No. 3,678,154, Jul. 18, 1972 to Widder et al., U.S. Pat. No. 5,338,537 issued Aug. 16, 1994 to White, Jr., and U.S. Pat. No. 5,451,401 issued Sep. 19, 1995 to Zerby et al.; carbonyl diphosphonates in U.S. Pat. No. 3,737,533, Jun. 5, 1973 to Francis; a zinc-polymer combination formed by the reaction or interaction of a zinc compound with an anionic polymer containing carboxylic, sulfonic and/or phosphonic acid radicals in U.S. Pat. No. 4,138,477, issued Feb. 6, 1979, to Gaffar; tartaric acid in U.S. Pat. No. 5,849,271 issued Dec. 15, 1998 and U.S. Pat. No. 5,622,689 issued Apr. 22, 1997 both to Lukacovic; acid or salt form of tartrate monosuccinate, tartrate disuccinate, and mixtures thereof in U.S. Pat. No. 5,015,467 issued May 14, 1991 to Smitherman; acrylic acid polymer or copolymer in U.S. Pat. No. 4,847,070, Jul. 11, 1989 to Pyrz et al. and in U.S. Pat. No. 4,661,341, Apr. 28, 1987 to Benedict et al.; sodium alginate in U.S. Pat. No. 4,775,525, issued Oct. 4, 1988, to Pera; polyvinyl pyrrolidone in GB 741,315 published Nov. 30, 1955, WO 99112517 published Mar. 18, 1999 and U.S. Pat. No. 5,538,714 issued Jul. 23, 1996 to Pink et al.; and copolymers of vinyl pyrrolidone with carboxylates in U.S. Pat. No. 5,670,138 issued Sep. 23, 1997 to Venema et al. and in JP Publication No. 2000-0633250 to Lion Corporation, published Feb. 29, 2000.

Dentifrices and mouthwashes containing soluble pyrophosphate salts have also been disclosed in the art, the pyrophosphates being indicated for a variety of purposes including as anticalculus agent. Included among such disclosures are U.S. Pat. No. 2,941,926, Jun. 21, 1960 to Salzmann et al.; U.S. Pat. Nos. 3,927,201 and 3,927,202, Dec. 16, 1975 to Baines et al. and Harvey et al., respectively;

U.S. Pat. No. 4,244,931, Jan. 13, 1981 and U.S. Pat. No. 4,247,526, Jan. 27, 1981 to Jarvis et al.; U.S. Pat. No. 4,515,772, May 7, 1985 to Parran, Jr. et al.; U.S. Pat. No. 5,180,576, Jan. 19, 1993 to Winston et al.; Japanese Patent Application No. 4945-1974; U.S. Pat. No. 4,323,551 issued Apr. 6, 1982, U.S. Pat. No. 4,515,772 issued May 7, 1985 and U.S. Pat. No. 4,885,155 issued Dec. 5, 1989 to Parran et al.; German Patent DE 39 42 644 B4, 1991; published February 28, international application WO 93/19728, published Oct. 14, 1993 and U.S. Pat. No. 4,822,599 issued Apr. 18, 1989 to Mitra. Also Draus, Lesniewski and Miklos disclose the in vitro effectiveness of soluble pyrophosphate salts against calculus in "Pyrophosphate and Hexametaphosphate Effects in Vitro Calculus Formation", Arch. Oral Biol., Vol. 15, pp. 893-896, (1970).

However, pyrophosphates are hardly to stabilize regarding both degradation and crystallization. This problem becomes even higher in aqueous solutions, such as mouthwashes. Thus, it is the object of the present invention to provide an aqueous solution, in particular in the form of a mouthwash or mouthrinse, which comprises pyrophosphates for calculus and stain prevention and which is stable in solution against crystallization, even if the composition was frozen and thawed up again.

SUMMARY OF THE INVENTION

Without being bound to a theory it was surprisingly found that pyrophosphate is stabilized in solution, in particular against crystallization, by formulating the pyrophosphate as a mixture of disodium pyrophosphate and tetrapotassium pyrophosphate in a special ratio in a special carrier solution, wherein the taste remains consumer acceptable.

According to one aspect there is provided a mouthwash or mouthrinse oral composition comprising at least about 0.5% by weight of the composition of pyrophosphate in an orally acceptable carrier, wherein the pyrophosphate is provided by a mixture of disodium pyrophosphate and tetrapotassium pyrophosphate in a ratio from disodium pyrophosphate to tetrapotassium pyrophosphate in the range of from about 1:0.4 to about 1:1.2 wherein the maximum level of cations in the composition is less than 300 mM and wherein the pH value of the composition is in the range of from about 6.0 to about 8.0. The orally acceptable carrier comprises preferably less than 11% alcohol.

According to another aspect there is disclosed the cosmetic use of a mouthwash or mouthrinse oral composition comprising at least about 0.5% by weight of the composition of pyrophosphate in an orally acceptable carrier, wherein the pyrophosphate is provided by a mixture of disodium pyrophosphate and tetrapotassium pyrophosphate in a ratio from disodium pyrophosphate to tetrapotassium pyrophosphate in the range of from about 1:0.4 to about 1:1.2 wherein the maximum level of cations in the composition is less than 300 mM and wherein the pH value of the composition is in the range of from about 6.0 to about 8.0 for anti-tartar and/or anti-calculus control. The orally acceptable carrier comprises preferably less than 11% alcohol.

According to another aspect there is provided a method for preventing and reducing stain and calculus formation by rinsing the oral cavity, in particular by rinsing the teeth and the mucosa with about 10 ml of a mouthwash or mouthrinse oral composition comprising at least about 0.5% by weight of the composition of pyrophosphate in an orally acceptable carrier, wherein the pyrophosphate is provided by a mixture of disodium pyrophosphate and tetrapotassium pyrophosphate in a ratio from disodium pyrophosphate to tetrapotassium pyrophosphate in the range of from about 1:0.4 to about 1:1.2 wherein the maximum level of cations in the composition is less than 300 mM and wherein the pH value of the composition is in the range of from about 6.0 to about 8.0 at least twice a day for at least about 60 sec. The orally acceptable carrier used comprises preferably less than 11% alcohol.

These and other features, aspects, and advantages of the present invention will become evident to those skilled in the art from the detailed description which follows.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated.

All measurements referred to herein are made at 22° C. (i.e. room temperature) unless otherwise specified.

As used herein, the word "about" means +/− 10 percent.

As used herein, the word "comprise," and its variants, e.g. "include", are intended to be non-limiting, such that recitation of items in a list is not to the exclusion of other like items that may also be useful in the materials, compositions, devices, and methods of this invention. This term encompasses the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The compositions herein are useful for topical application, in particular for topical application in the mouth. I.e. the composition might be an oral care composition. As used herein, "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. Oral care composition may be generally in various forms including toothpaste, dentifrice, tooth gel, subgingival gel, mouthrinse, mouthwash, mouthspray, mousse, foam lozenge, chewable tablet, chewing gum or denture product. The oral composition disclosed herein is preferably provided in the form of an aqueous solution, i.e. the oral composition disclosed herein is preferably provided in the form of a mouthrinse, a mouthwash or a mouthspray.

Herein, the terms "tartar" and "calculus" are used interchangeably and refer to mineralized dental plaque biofilms.

The term "teeth", as used herein, refers to natural teeth as well as artificial teeth or dental prosthesis and is construed to comprise one tooth or multiple teeth.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed. The mouthwashes or rinses as disclosed herein may also include one or more of actives materials.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. The carriers or excipients of the present invention can include the usual and conventional components of mouthwashes or rinses, as more fully described hereinafter: Mouthwash or rinse carrier materials typically include, but are not limited to one or more of water, alcohol, humectants, surfactants, and acceptance improving agents, such as flavoring, sweetening, coloring and/or cooling agents. The preferred embodiments of the subject invention are mouthwashes or rinses comprising for example as carrier material, one or more of water, ethanol, a humectant, a surfactant, a flavoring agent, a sweetening agent, a coloring agent and optionally a cooling agent. In particular the carrier material comprises the mixture of water, ethanol, a humectant, a surfactant, a flavoring agent, a sweetening agent, and a coloring agent. Optionally mouthwash or rinse carrier materials comprise in addition preservatives, buffering agents and mixtures thereof. Typical mouthwash or rinse carrier materials are for example also disclosed in, e.g., U.S. Pat. No. 3,988,433 to Benedict. Preparation of such compositions are well known in the art and their selection will depend on secondary considerations like taste, cost, and shelf stability, etc.

The preferred embodiments of the subject invention are mouthwashes or rinses comprising for example as active materials one or more anticalculus/anti-tartar agent. In addition, the preferred embodiments of the subject invention are mouthwashes or rinses comprising for example as active materials an anticalculus/anti-tartar agent and an anticaries agent. A suitable anticalculus/anti-tartar agent may be for example a pyrophosphate source present in a concentration sufficient to provide the intended effect. A suitable anticaries agent may be for example a fluoride ion source present in a concentration sufficient to provide the intended effect.

Sufficient amounts of fluoride ions to provide anticaries effectiveness are in the range from about 0.0025% to about 5.0% by weight, preferably from about 0.005% to about 2.0% by weight of the composition. A wide variety of fluoride ion-yielding materials can be employed as sources of soluble fluoride in the present compositions and methods. Examples of suitable fluoride ion-yielding materials are found in U.S. Pat. No. 3,535,421 to Briner et al. and U.S. Pat. No. 3,678,154 to Widder et al. Suitable fluoride ion sources comprise, but are not limited to stannous fluoride, sodium fluoride, potassium fluoride, sodium monofluorophosphate, indium fluoride, amine fluorides such as Olaflur, and mixtures thereof. In particular, the fluoride compound used in the mouthwashes disclosed herein is sodium fluoride or stannous fluoride. If a sodium free fluoride ion source is chosen, potassium fluoride is preferred.

The present compositions comprise a pyrophosphate salt as a source of pyrophosphate ions to provide the anticalculus and anti-tartar effect. The pyrophosphate salts useful in the present compositions include the dialkali metal pyrophosphate salts, tetraalkali metal pyrophosphate salts, and mixtures thereof, in their unhydrated as well as hydrated forms. For example disodium dihydrogen pyrophosphate ($Na_2H_2P_2O_7$) and tetrapotassium pyrophosphate ($K_4P_2O_7$) are the preferred species. Pyrophosphate salts are described in more detail in *Kirk-Othmer Encyclopedia of Chemical Technology*, Third Edition, Volume 17, Wiley-Interscience Publishers (1982).

In compositions of the present invention, the pyrophosphate salts are completely dissolved and are stable against crystallization in solution, even, after the composition was frozen and thawed up again. Therefore, the pyrophosphate sources are present in the mouthwashes as disclosed herein in a special ratio and a special mixture. Surprisingly, a special mixture of dialkali metal and tetraalkali metal pyrophosphates was found to be particularly stable in solution. In addition, the bitter taste which is caused by the use of tetrapotassium pyrophosphate is at a level which is acceptable by the consumer. The preferred mixture of disodium pyrophosphate and tetrapotassium pyrophosphate being in a ratio from disodium pyrophosphate to tetrapotassium pyrophosphate in the range of about 1:0.4 to about 1:2.4 was found to be stable against crystallization. "To be stable against crystallization" shall mean herein that the pyrophosphate is completely soluble and does not build any crystals even if the solution was frozen and thawed up again. Preferably, the ratio from disodium pyrophosphate to tetrapotassium pyrophosphate is in the range from about 1:0.8 to about 1:2.2, more preferred in the range from about 1:1.0 to about 1:2.0 and most preferred in the range from about 1:1.05 to about 1:1.5 in order to further increase the stability against crystallization.

The stability against crystallization can be measured as crystal prevention score (CPS). The CPS corresponds to the time needed until a composition gets crystal free after being frozen completely. During thawing the test bottles are secured against any movement or other mechanical influence. Detailed experimental description is given below in the experimental section. The CPS used in the present invention is based on the scoring according to the following table:

| | Crystal free after [days] | |
|---|---|---|
| CPS | At RT | At 2-5° C. |
| 100 | 5-6 hr | 1 |
| 90 | 1 | 2 |
| 80 | 2 | 3 |
| 70 | 3 | 4 |
| 60 | 4 | ND |
| 50 | ND | 7 |
| 30 | 7 | 14 |
| 10 | 14 | 28 |
| 0 | >14 | >28 |

ND: Not done

The mouthwash or mouthrinse oral compositions of the present invention are formulated in order to be stable against crystallizations. Thus, the compositions of the present invention show high crystal prevention score (CPS), in particular CPS in the range of from 70 to 100, preferably from 85 to 100, more preferred from 90 to 100, most preferred from 95 to 100.

Free pyrophosphate ions may be present in a variety of protonated states depending on the pH of the composition. By formulating the pyrophosphate level in an oral composition the degradation of the pyrophosphate in solution have to be considered. The final amount of free pyrophosphate ions in the mouthwash is at least about 0.5% by weight of the composition. For the intended anticalculus and anti-tartar effect an amount of free pyrophosphate of at least about 0.5% by weight of the composition is sufficient for the mouthwashes or mouthrinses as disclosed herein, wherein the choice of the counter ion does not influence the anticalculus and anti-tartar efficacy. However, solubilized pyrophosphates are principally subjected to degradation over time. Thus, it might be advantageous to formulate higher amounts of pyrophosphates into the present compositions, for example, the amount of pyrophosphate may be at least about 1.0% or at least about 1.3% or at least about 1.6% by weight of the composition depending on the intended storage life time. Suitable maximal levels of pyrophosphate in the composition are maximal 2.8% by weight of the composition, preferably maximal 2.5% by weight of the composition, more preferred maximal 2.3% by weight of the composition. The upper limit of the pyrophosphate in the composition considers the crystallization potential of the pyrophosphate with suitable counter-ions as well as the products taste.

The degradation of the pyrophosphates is for example influenced by the pH value and the storage temperature of the composition. The lower the pH value and the higher the storage temperature the higher is the pyrophosphate degradation. The pH value of the present composition is in the range from about 6 to about 8, in particular in the range from about 6.5 to about 7.5. Without being bound to a theory it is believed that the pH value of the present composition does not only influences the pyrophosphate degradation, but also further stabilizes the pyrophosphates in solution. The pH value of the mouthwashes as disclosed herein can be adjusted by combining the actives and the orally acceptable carrier in the preferred ranges. If necessary, buffer material can be added in order to adjust the pH value to the disclosed ranges, but preferably, the mouthwash compositions as disclosed herein are formulated without adding buffer agents. In particular, the mouthwash compositions as disclosed herein do not comprise any acidic pH value adjuster.

For stabilizing the pyrophosphate ions in solution, in particular in mouthwash or mouthrinse solution as disclosed herein, the total amount of cations, in particular sodium and potassium has to be considered as well. Sodium pyrophosphate shows a lower solubility in product matrix than the other alkali metal pyrophosphates. Potassium pyrophosphate imparts a bitter taste to the composition. Thus, it is preferred, to control the maximum level of cations, in particular of sodium and potassium in the total composition. In particular, the maximum level of cations, preferably sodium and potassium in the composition as disclosed herein should be less than about 300 mM, preferably less than about 280 mM and more preferred less than about 270 mM. Further, said limitation, in particular the limitation of the sodium level helps to formulate the intended pH value without adding further pH-adjuster. In addition, the maximum level of potassium in the composition as disclosed herein should be less than about 210 mM, preferably less than about 180 mM and more preferred less than about 150 mM in order to achieve an acceptable taste. Thus, in order to achieve a stable and good tasting composition the choice of counter ions for the pyrophosphate in the composition as well as the overall level has to be done carefully.

In addition, the carrier material of the mouthwash compositions as disclosed herein is adapted to further stabilize the pyrophosphate ions in solution. By influencing the dielectric constant of the final solution the pyrophosphate solubility can be increased by increasing the dielectric constant. Therefore, carrier compounds that influence the dielectric constant are chosen accordingly and limited in its amount.

For example, it is believed that the amount and choice of the humectant used in the carrier material may further stabilize the pyrophosphate ions against crystallization in solution. The humectant serves to give compositions a moist feel to the mouth. Suitable humectants for use in compositions of the subject invention include edible polyhydric alcohols such as glycerin, sorbitol, xylitol, butylene glycol, polyethylene glycol, propylene glycol and trimethyl glycine or mixture thereof, wherein glycerin, propylene glycol, sorbitol (70% solution) or a mixture thereof is preferred. In addition, the maximum amount of the humectant should be limited. A maximum amount of about 8% by weight of the composition is preferred for the present compositions and the minimal amount should not be less than about 4% by weight of the composition. Thus, the mouthwash compositions as disclosed herein comprises preferably a humectant in the range of from about 4% to about 8%, more preferred in the range of from about 4.5% to about 7%, more preferred in the range of from about 5% to about 6% by weight of the composition.

In addition or alternatively, it was surprisingly found that although alcohol reduces the freezing temperature of the solution the maximum level of alcohol should be restricted in order to stabilize the pyrophosphates in mouthwash or mouthrinse solutions. In a preferred embodiment the composition as disclosed herein comprises less than about 11% alcohol, i.e. ethanol, by weight of the composition. More preferred the amount of ethanol should be below about 9% and most preferred the amount of ethanol should be in the range of about 8% to about 9% by weight of the composition. When the level of alcohol is reduced below 8% by weight of the composition further preservatives should be included into the composition. Generally, a composition which is free of further preservatives is preferred. Without being bound to a theory it is believed that the ethanol is critical for micro efficacy, influences the stability of the pyrophosphate against crystallization and influences taste, e.g. the burning sensation and consumer acceptance of the whole composition.

The present compositions may also comprise surfactants, also commonly referred to as sudsing agents. Suitable surfactants are those which are reasonably stable and foam throughout a wide pH range. The surfactant may be anionic, non-ionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isothionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The composition may typically comprise an anionic surfactant at a level of from about 0.01% to about 5%, from about 0.01% to about 2% in some embodiments, and from about 0.01% to about 1% in other embodiments by weight of the composition. Another suitable surfactant is one selected from the group consisting of sarcosinate surfactants, isothionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate.

Useful cationic surfactants include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyl-trimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current composition, are not preferred due to their capacity to stain the oral cavity's hard tissues. Persons skilled in the art are aware of this possibility and should incorporate cationic surfactants only with this limitation in mind.

Nonionic surfactants that can be used in the compositions include compounds produced by the condensation of alkylene oxide groups (hydrophilic in nature) with an organic hydrophobic compound which may be aliphatic or alkylaromatic in nature. Examples of suitable nonionic surfactants include polysorbates, which are derived from PEG-ylated sorbitan esterified with fatty acids or poloxamers which are difunctional block-polymers terminating in primary hydroxyl groups with molecular weights ranging from 1,000 to above 15,000. Poloxamers are e.g. sold under the tradename of Pluronics and Pluraflo by BASF. The Pluronics are polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. Suitable poloxamers for this invention are Poloxamer 407 and Pluraflo L4370 which may also function as an emulsifying agent, binder, stabilizer, and other related functions. The nonionic surfactant may be present in the compositions from about 0.1% to about 5%, preferably from about 0.01% to about 2.0% preferably from about 0.01% to about 1.0% by weight of the total composition.

Useful zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water-solubilizing group, e.g. carboxy, sulfonate, sulfate, phosphate or phosphonate. Suitable betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, cocobetaine or 2-(N-coc-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine. The composition may typically comprise a zwitterionic surfactant at a level of from about 0.01% to about 5%, from about 0.01% to about 2% in some embodiments, and from about 0.01% to about 1% by weight of the composition.

The present composition further comprises one or more acceptance improving agents which are formulated into the composition in order to improve the taste, the optics or any other property of the composition which improves the acceptance of the composition by the consumer. Suitable acceptance improving agents are for example sweetening agents, coloring agents, flavoring agents, optionally cooling agents or a mixture thereof.

Sweetening agents which can be used include sucrose, glucose, saccharin, sucralose, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate, sucralose and sodium saccharin, and mixtures thereof. A composition preferably contains from about 0.01% to about 2.0% by weight of the composition of these agents, more preferred from about 0.01% to about 1% of these agents, more preferred from about 0.01% to about 0.1%, by weight of the composition of the sweetening agents.

Flavoring agents may also be added to the compositions. Examples of suitable flavoring agents as disclosed in U.S. Pat. No. 4,684,517 to Clipper et al. include menthol, methyl salicylate, cinnamic aldehyde and clove oil. Generally, plant oils, such as peppermint or spearmint oil are often used in oral care compositions. Flavoring agents are generally used in the compositions at levels of from about 0.001% to about 2%, preferably from about 0.05% to about 1%, more preferred from about 0.1% to about 0.5% by weight of the composition.

In addition to sweetening and flavoring agents or as part of the flavoring agents cooling agents, salivating agents, warming agents, and numbing agents can be used as optional ingredients in the compositions. These agents are present in the compositions at a level of from about 0.001% to about 2%, preferably from about 0.01% to about 1%, by weight of the composition.

The cooling agent can be any of a wide variety of materials. Included among such materials are carboxamides, menthol, ketals, diols, and mixtures thereof. Preferred cooling agents in the present compositions are the paramenthan carboxyamide agents such as N-ethyl-p-menthan-3-carboxamide, known commercially as "WS-3", N,2,3-trimethyl-2-isopropylbutanamide, known commercially as "WS-23," Ethyl 3-(p-menthane-3-carboxamido)acetate known commercially as "WS-5", (1R,2S,5R)—N-(4-Methoxyphenyl)-p-menthanecarboxamide known commercially as "WS-12", (1R,2S,5R)—N-(4-(cyanomethyl)phenyl)menthylcarboxamide known commercially as "G-180" and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Suitable salivating agents include Jambu® manufactured by Takasago. Examples of warming agents are capsicum and nicotinate esters, such as benzyl nicotinate. Suitable numbing agents include benzocaine, lidocaine, clove bud oil, and ethanol.

The coloring agents can be any of a wide variety of materials. Any orally acceptable coloring agent can be used depending on the intended color. The coloring agent can be added as solid or liquid. Suitable coloring agents are for example blue or green colors. These agents are present in the compositions e.g. at a level of from about 0.0001% to about 0.2%, preferably from about 0.0001% to about 0.1%, more preferred from about 0.0001% to about 0.01% by weight of the composition.

The oral compositions as disclosed herein are mouthwash or mouthrinse compositions. Thus, the compositions are aqueous solutions and comprise a main amount of water in the carrier. Suitable amounts of water are for example in the range of from 60% to 95%, preferably from 65% to 90%, more preferred from 70% to 85% by weight of the composition.

In the following a few example embodiments are given of suitable carrier(s) for the oral mouthwash compositions as disclosed herein. The mouthwashes or rinses comprising for example as carrier material from 60% to 95% of water, less than 12% ethanol, from 4% to 8% of a humectant, from 0.01% to 5% of a surfactant, from 0.01% to 2% of a flavoring agent, from 0.01% to 2% of a sweetening agent and from 0.0001% to 0.2% of a coloring agent by weight of the composition or a mixture of one or more of these carrier materials. In particular, the carrier materials of the mouthwashes or rinses as disclosed herein may comprise for example a mixture of from 65% to 90% of water, less than 11% ethanol, from 4.5% to 7% of a humectant, from 0.01% to 2% of a surfactant, from 0.05% to 1% of a flavoring agent, from 0.01% to 1% of a sweetening agent and from 0.0001% to 0.1% of a coloring agent by weight of the composition or a mixture of one or more of these carrier materials. Further preferred suitable carrier materials for the mouthwashes or rinses as disclosed herein may comprise a mixture of from 70% to 85% of water, from 8% to 9% ethanol, from 5% to 6% of a humectant, from 0.01% to 1% of a surfactant, from 0.1% to 0.5% of a flavoring agent, from 0.01% to 0.1% of a sweetening agent and from 0.0001% to 0.01% of a coloring agent by weight of the composition.

These example carrier mixtures may be for example combined with active materials providing e.g. anticalculus/anti-tartar effects, such as a mixture of disodium pyrophosphate and tetrapotassium pyrophosphate in a ratio from disodium pyrophosphate to tetrapotassium pyrophosphate in the range of about 1:0.4 to about 1:2.4, wherein the composition comprises a pH in the range of from about 6.0 to about 8.0. In particular, the example carrier mixtures may be combined with active materials such as a mixture of disodium pyrophosphate and tetrapotassium pyrophosphate in a ratio from disodium pyrophosphate to tetrapotassium pyrophosphate in the range of from about 1:1.05 to about 1:1.5, wherein the composition comprises a pH in the range of from about 6.5 to about 7.5.

If anticaries benefits shall be provided in addition, an anticaries agent can be combined with the anticalculus agents. Thus, these example carrier mixtures may be for example combined with active materials such as at least about 0.0025% by weight of the composition of fluoride ions and a mixture of disodium pyrophosphate and tetrapotassium pyrophosphate in a ratio from disodium pyrophosphate to tetrapotassium pyrophosphate in the range of about 1:0.4 to about 1:2.4, wherein the composition comprises a pH in the range of from about 6.0 to about 8.0. In particular, the example carrier mixtures may be combined with active materials such as at least about 0.005% by weight of the composition of fluoride ions and a mixture of disodium pyrophosphate and tetrapotassium pyrophosphate in a ratio from disodium pyrophosphate to tetrapotassium pyrophosphate in the range of from about 1:1.05 to about 1:1.5, wherein the composition comprises a pH in the range of from about 6.5 to about 7.5.

As the present composition provides anti-tartar and/or anti-calculus control benefits the disclosed compositions can be used for anti-tartar and/or anti-calculus control. For controlling tartar and preventing staining of the teeth a subject's dental enamel surfaces and mucosa in the mouth should be contacted with the oral compositions according to the present invention. Contacting may be rinsing with a mouthwash or mouthrinse. The subject may be any person or animal whose tooth surface contacts the oral composition. By animal is meant to include household pets or other domestic animals, or animals kept in captivity. Example would include the rinsing of a cat's mouth with an oral composition for a sufficient amount of time to see a benefit. A benefit can be for example seen by rinsing the dental enamel surfaces and mucosa twice a day for at least 30 sec with the 20 ml of the composition as disclosed herein alternatively by rinsing the dental enamel surfaces and mucosa twice a day for at least 60 sec with 10 ml product.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example I: Crystal Prevention Score (CPS)

The stability against crystallization can be measured as crystal prevention score (CPS). The CPS corresponds to the time needed until a composition gets crystal free after being frozen completely. For determining the CPS the composition in multiple 500 ml clear bottles (3-6 bottles per composition) to be tested is frozen at lower than −18° C. for at least 24 h. Then these bottles are transferred to room temperature or/and to a 2-5° C. refrigerator and the time until all bottles get crystal free is measured. During thawing these bottles are secured against any movement or other mechanical influence. Some of the experiments are repeated 2-3 times. Results will be averaged, if not all bottles of the same composition get crystal free at the exactly same time. Therefore, the results are averaged and the CPS is determined according to the following table:

| CPS | Crystal free after [days] | |
| --- | --- | --- |
| | At RT | At 2-5° C. |
| 100 | 5-6 hr | 1 |
| 90 | 1 | 2 |
| 80 | 2 | 3 |
| 70 | 3 | 4 |
| 60 | 4 | ND |
| 50 | ND | 7 |

-continued

| CPS | Crystal free after [days] | |
|---|---|---|
| | At RT | At 2-5° C. |
| 30 | 7 | 14 |
| 10 | 14 | 28 |
| 0 | >14 | >28 |

ND: Not done

Example II: Mouthwash Compositions

Mouthwash compositions according to the present invention (Examples IA-ID) are shown below with amounts of components in % by weight of the composition. These compositions are made using conventional methods, in particular as given in Example III. The CPS for each composition was measured and is given below.

| Ingredient | Ex. IA | Ex. IB | Ex. IC | Ex. ID | Comparative Example |
|---|---|---|---|---|---|
| Sodium Fluoride | 0.02 | 0.02 | 0.02 | 0.02 | 0.02 |
| Disodium pyrophosphate | 1.06 | 1.04 | 1.17 | 1.06 | 0.66 |
| Tetrasodium pyrophosphate | — | — | — | — | 1.64 |
| Tetrapotassium pyrophosphate (60% solution) | 2.38 | 2.42 | 2.13 | 2.88 | — |
| Glycerine | 5.0 | 5.0 | 5.0 | 5.0 | 7.5 |
| Poloxamer 407 | 0.12 | 0.12 | 0.12 | 0.12 | 0.12 |
| Polysorbate 80 | 0.31 | 0.31 | 0.31 | 0.31 | 0.31 |
| Sodium saccharin | 0.03 | 0.03 | 0.03 | 0.03 | 0.03 |
| Sucralose | 0.01 | 0.01 | 0.01 | 0.01 | 0.01 |
| flavor | 0.15 | 0.15 | 0.15 | 0.15 | 0.15 |
| Ethanol | 10.8 | 10.8 | 10.8 | 10.8 | 10.8 |
| Citric acid | — | — | — | — | 0.204 |
| Dye | 0.0002 | 0.0002 | 0.0002 | 0.0002 | 0.0002 |
| Water | QS | QS | QS | QS | QS |
| pH | 7.0 | 7.1 | 6.75 | 7.5 | 7.0 |
| CPS RT (2-5° C.) | 100 (100) | 100 (100) | 100 (ND) | 100 (ND) | 13 (0) |

ND: Not done

Example III: Preparation of the Mouthwash

One suitable method is given to manufacture the compositions as disclosed herein. Deviations of said method and alternatives are possible and can be considered by the skilled person. The dye is solved in a part of the water in order to form a dye premix. For solving the dye completely the dye premix is agitated for at least 10 min without splashing. In parallel a flavor premix is produced by adding the flavors into the ethanol under continuous agitation without splashing. Then a part of the surfactant is added to the flavor premix and the flavor premix is agitated for at least 10 min. Then the remaining water is added in a main mix tank where water temperature is maintained between 20 to 30° C. Under continuous agitation without splashing first the tetrapotassium pyrophosphate followed by the disodium pyrophosphate is added slowly in order to avoid clumping. After at least 5 min of agitation, the rest of the surfactant, sweeteners and sodium fluoride are added under moderate agitation so that excessive foam formation is avoided. Then the agitation speed is further reduced and the glycerin is added to the main mix followed by the dye premix and the flavor premix. The final composition is then mixed for at least 20 min until a homogeneous composition is received.

Example IV: Consumer Acceptance

Example IA was tested against the comparative Example which is a product currently on the market regarding the overall performance and consumer acceptance by 12 people who were willing to use a mouthwash. Blind paired comparison tests were performed at three days. In each category people were asked to give their rate of agreement with the questions asked:
 1. Direct Question (DQ) scale: 0 means poor, 100 means excellent.

| Category [Scale, 0-100] | Example IA | Comparative Example |
|---|---|---|
| "Overall acceptance" | 43 | 45 |
| "Is enjoyable to use" | 47 | 60 |
| "Has an appealing taste" | 53 | 50 |
| Leaves pleasant taste in mouth | 41 | 43 |

2. Intensity Rating scale: 0 means no agreement, 10 means full agreement.

| Category [Scale, 0-10] | Example IA | Comparative Example |
|---|---|---|
| "Has a burning sensation" | 6.9 | 5.9 |
| "Has a bitter taste" | 4.1 | 4.0 |
| "Has a metallic aftertaste" | 3.9 | 2.1 |
| "Has a cooling sensation" | 6.1 | 5.9 |

Example IA was found by the consumer to be equal in the overall acceptance to the comparative example. The taste was considered being slightly better. Burning sensation, bitterness and cooling sensation are slightly increased. This might be the reason why Example IA is rated to be less enjoyable to use although the taste was scored better compared to the Comparative Example. In summary, the consumer acceptance of Example IA is at least as good as for the Comparative Example on the market.

In a second test trained sensory panelists compared Example IA and the Comparative Example regarding burning sensation and bitterness.

| | Example IA | Comparative Example |
|---|---|---|
| Intensity of the Burning sensation [Scale 0-60] | | |
| In mouth | 23.9 | 25 |
| After expectoration | 20.3 | 20.8 |
| Intensity of the Bitterness [Scale 0-60] | | |
| In mouth | 8.4 | 6.5 |
| After expectoration | 15.3 | 13.8 |
| After 5 min | 4.4 | 6.9 |

The trained panelists sensed less burning for Example IA compared to the Comparative Example, but the sensation of bitterness was slightly increases for Example IA. However, in long term consideration, i.e. after 5 min bitterness of Example IA is less than compared to the Comparative Example. That means, even if the effect is small the compositions as disclosed herein show also taste advantages, e.g.

a faster bitterness decrease, compared to the Comparative Example in addition to the stabilization against crystal formation in solution.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A mouthwash oral composition comprising at least 0.5% by weight of the composition of pyrophosphate in an orally acceptable carrier, wherein the pyrophosphate is provided by a mixture consisting of disodium pyrophosphate and tetrapotassium pyrophosphate in a ratio from disodium pyrophosphate to tetrapotassium pyrophosphate in the range of 1:0.4 to 1:2.4 and wherein the pH of the composition is in the range of 6.0 to 8.0, wherein the orally acceptable carrier comprises less than 11% alcohol, wherein the maximum level of potassium in the composition is less than 210 mM.

2. The mouthwash composition according to claim 1, wherein the orally acceptable carrier comprises less than 9% alcohol by weight of the composition.

3. The mouthwash composition according to claim 2, wherein the orally acceptable carrier comprises alcohol in the range of 8% to 9% by weight of the composition.

4. The mouthwash composition according to claim 1, wherein the orally acceptable carrier comprises from 60% to 95% water by weight of the composition.

5. The mouthwash composition according to claim 4, wherein the orally acceptable carrier comprises from 70% to 85% water by weight of the composition.

6. The mouthwash composition according to claim 1, wherein the orally acceptable carrier comprises a humectant.

7. The mouthwash composition according to claim 6, wherein the orally acceptable carrier comprises at least one of glycerin, propylene glycol, or sorbitol.

8. The mouthwash composition according to claim 6, wherein the composition comprises the humectant in the range of 4% to 8% by weight of the composition.

9. The mouthwash composition according to claim 1, wherein the composition comprises at least 1.0% pyrophosphate by weight of the composition.

10. The mouthwash composition according to claim 1, wherein the composition comprises at least 1.6% pyrophosphate by weight of the composition.

11. The mouthwash oral composition according to claim 1, wherein the maximal amount of the pyrophosphate in the composition is 2.8% by weight of the composition.

12. The mouthwash oral composition according to claim 11, wherein the maximal amount of the pyrophosphate in the composition is 2.3% by weight of the composition.

13. The mouthwash composition according to claim 1, wherein the pH of the composition is in the range from 6.5 to 7.5.

14. The mouthwash composition according to claim 1, wherein the ratio from disodium pyrophosphate to tetrapotassium pyrophosphate is in the range from 1:0.8 to 1:2.2.

15. The mouthwash composition according to claim 14, wherein the ratio from disodium pyrophosphate to tetrapotassium pyrophosphate is in the range from 1:1.0 to 1:2.0.

16. The mouthwash composition according to claim 1, wherein the composition comprises a fluoride ion source.

17. The mouthwash composition according to claim 1, wherein the composition further comprises an acceptance improving agent.

18. The mouthwash composition according to claim 1, wherein the composition comprises a crystal prevention score (CPS) in the range of from 80 to 100.

* * * * *